(12) United States Patent
Shirai et al.

(10) Patent No.: US 7,105,717 B1
(45) Date of Patent: Sep. 12, 2006

(54) MODEL RAT WITH THE ONSET OF PROSTATIC CANCER

(75) Inventors: Tomoyuki Shirai, Nagoya (JP); Makoto Asamoto, Nagoya (JP); Satoru Takahashi, Nagoya (JP)

(73) Assignee: Japan Science and Technology Agency, Saitama (JP)

( * ) Notice: Subject to any disclaimer, the term of this patent is extended or adjusted under 35 U.S.C. 154(b) by 394 days.

(21) Appl. No.: 10/204,504

(22) PCT Filed: Jun. 13, 2000

(86) PCT No.: PCT/JP00/03825

§ 371 (c)(1),
(2), (4) Date: Aug. 20, 2002

(87) PCT Pub. No.: WO01/60151

PCT Pub. Date: Aug. 23, 2001

(30) Foreign Application Priority Data

Feb. 21, 2000 (JP) ............................. 2000-042491

(51) Int. Cl.
A01K 67/00 (2006.01)
(52) U.S. Cl. ................................. 800/8; 800/3; 800/21
(58) Field of Classification Search ................. 800/21, 800/8, 3
See application file for complete search history.

(56) References Cited

U.S. PATENT DOCUMENTS 5,907,078 A * 5/1999 Greenberg et al. ............ 800/10

OTHER PUBLICATIONS

Navone et al. (1999) Model Systems of prostate Cancer: USes and Limitations. Cancer and Metastatsis Reviews. 17:361-371.*
Drago et al. (1980) The Nb rat prostatic adenocarcinoma model system. Prog. Clin. Biol. Res. 37:265-91. (Abstract only).*
T. Shirai, et al. *Rat Prostate As One of the Target Organs for 3,2'-Dimethyl-4-aminobiphenyl-Induced Carcinogenesis: Effects of Dietary Ethinyl Estradiol and Methyltestosterone.* Jpn. J. Cancer Res., vol. 76, pp. 803-808, Sep. 1985.
T. Shirai, et al. *Induction of Invasive Carcinomas in the Accessory Sex Organs Other Than the Ventral Prostate of Rats Given 3,2'-Dimethyl-4-aminobuphenyl and Testosterone Propionate.* Cancer Research. vol. 51, pp. 1264-1269, Feb 15, 1991.
T. Shirai, et al. *Duration dependent induction of invasive prostatic carcinomas with pharmacological dose of testosterone propionate in rats pretreated with 3,2'-dimethyl-4-aminobiphenyl and development of androgen-independent carcinomas after castration.* Cancer Letters. vol. 83, pp. 111-116, 1994.
T. Shirai, et al. *Site-specific Effects of Testosterone Propionate on the Prostate of Rat Pretreated with 3,2'-Dimethyl-4-Aminobiphenyl: Dose-dependent Induction of Invasive Carcinomas.* Jpn. J. Cancer Res., vol. 86, pp. 645-648, Jul. 1995.
T. Masui, et al. *Ki-ras Mutations With Frequent Normal Allele Loss Versus Absence of p. 53 Mutations in Rat Prostate and Seminal Vesicle Carcinomas Induced With 3,2'-Dimethyl-4-aminobiphenyl.* Molecular Carcinogenesis. vol. 13, pp. 21-26, 1995.
H. Nakanishi, et al. *Establishment and Characterization of Three Androgen-independent, Metastatic Carcinoma Cell Lines from 3,2'-Dimethyl-4-aminobiphenyl-induced Prostatic Tumors in F344 Rats* Jpn. J. Cancer Res. vol. 87, pp. 1218-1226, Dec. 1996.
K. Kato, et al. *Establishment of Transplantable Rat Prostate Carcinomas from Primary Lesions Induced by 3,2'-Dimethyl-4-aminobiphenyl and Testosterone.* J. Toxicol. Pathol., vol. 11, pp. 27-32, 1998.
S. Iwasaki, et al., *Development of Androgen-independent Carcinomas from Androgen-dependent Preneoplastic Lesions in the male Accessory Sex Organs of Rats Treated with 3,2'-Dimethyl-4-aminobiphenyl and Testosterone Propionate.* Jpn. J. Cancer Res., vol. 90, pp. 23-30, Jan. 1999.
J.W.Gordon, et al., *Genetic transformation of mouse embryos by microinjection of purified DNA.* Proc. Natl. Acad. Sci. USA. vol. 77, No. 12, pp. 7380-7384, Dec. 1980.
Y. Toyoda, et al., *Fertilization of Rat Eggs IN VITRO By Epididymal Spermatozoa and the Development Eggs Following Transfer.* J. Reprod. Fert., vol. 36, pp. 9-22, 1974.
Nihon gan gakkai soukai kiji (Article on the 58th Annual Meeting of Japanese Cancer Association), p. 406, 1999.
B. Charreau, et al. *Transgenesis in rats:technical aspects and models.* Transgenic Research. vol. 5, pp. 223-234, 1996.
Proceedings of the American Association for Cancer Research, Abstracts, vol. 41, p. 47, Mar. 2000.
Annual Meeting Abstracts., Laboratory Investigation, vol. 76, No. 1, p. 70A, 1997.
S. Kasper, et al., *Development, Progression, and Androgen-Dependence of Prostate Tumors in Probasin-Large T-Antigen Transgenic Mice: A Model for Prostate Cancer.* Laboratory Investigation. vol. 78, No. 3, pp. 319-333, 1998.
J. E. Green, et al., *Workgroup 3: Transgenic and Reconstitution Models of Prostate Cancer.* The Prostate. vol. 36, pp. 59-63, 1998.
S. Hochi, et al., *Successful Production of Transgenic Rats.* Animal Biotechnology. vol. 1, No. 2, pp. 175-184, 1990.

(Continued)

Primary Examiner—Deborah Crouch
Assistant Examiner—Louis D. Lieto
(74) Attorney, Agent, or Firm—Morgan & Finnegan, L.L.P.; Kenneth H. Sonnenfeld; Michael A. Willis (57) ABSTRACT

To provide a rat model with the onset of prostate cancer in which the prostate cancer including an invasive cancer can be developed and can be bred for generations stably. A rat model with the onset of prostate cancer which can develop prostate cancer including invasive cancer and can be bred for generations stably is established by: ligating an SV40 large T antigen gene onto the downstream of rat probasin gene promoter; the resulting PBSVT transgene is introduced into a fertilized egg of a Sprague-Dawley rat; after the introduction, the fertilized egg is transplanted into a recipient rat; a transgenic rat obtained from the recipient rat is then mated with a wild-type Sprague-Dawley rat; the transgenic offspring rats thus obtained are similarly can be bred for generations thereafter; and transgenic rats developing prostate cancer are selected through histopathological observation of the prostate.

7 Claims, 1 Drawing Sheet

OTHER PUBLICATIONS

S.V. Garde, et al., *A comparative study on expression of prostatic inhibin peptide, prostate acid phosphatase and prostate specific antigen in androgen independent human and rat prostate carcinoma cell lines*. Cancer Letters. vol. 70, pp. 159-166, 1993.

Takahashi et al., "Tumor development in transgenic rats harboring probasin gene promoter/SV40 T antigen fusion gene," Nihon gan gakkai soukai kiji (Article on the 58th Annual Meeting of Japanese Cancer Association), p. 406, Aug. 30, 1999.

Greenberg et al., "Prostate Cancer in a Transgenic Mouse," Proc. Natl. Acad. Sci., vol. 92, pp. 3439-3443, Apr. 1995.

Patent Abstracts of Japan, English language abstract of JP 11-313575, published Nov. 16, 1999.

Greenberg et al., "Prostate Cancer in a Transgenic Mouse," Proc. Natl. Acad. Sci., vol. 92, pp. 3439-3443, Apr. 1995.

Patent Abstracts of Japan, English language abstract of JP 11-313575, published Nov. 16, 1999.

\* cited by examiner

FIG. 1

MODEL RAT WITH THE ONSET OF PROSTATIC CANCER

TECHNICAL FIELD

The present invention relates to rat models with the onset of prostate cancer which can develop prostate cancer including invasive cancer can be bred for generations stably, and to methods of establishing the same. More specifically, the invention relates to rat models with the onset of prostate cancer introduced with an SV (simian virus) 40 large T antigen gene which is under the control of probasin gene promoter, wherein the rat model can develop prostate cancer including invasive cancer in almost all the cases by the age of 15 weeks and can be bred for generations stably, and is particularly related to the PBSVT transgenic rat 2971 lines and to methods of establishing the rat. The present invention also relates to screening methods or the like for a substance promoting the onset and/or progress of, or suppressing the onset and/or progress of prostate cancer, where the rat model with the onset of prostate cancer is used.

RELATED ARTS

Prostate cancer is the second most common cause among cancer deaths in Western countries. In Japan, prostate cancer currently remains the eleventh cause of cancer deaths. However, with the prolonged average life expectancy, the number of prostate cancers is expected to increase rapidly. While the etiology of prostate cancer is largely unknown, it is androgen-dependent in its early stages, and then acquires independency, which will acquire drug-resistance. In order to elucidate the developmental mechanism of prostate cancer that undergoes such multiple stages, animal models of prostate cancer generated from various species and from various lines are needed. Several types of animal models for prostate cancer have been generated and have been utilized to elucidate the developmental mechanism of prostate cancer and its modifiers. A previous report shows that a long latent period of approximately 20 months is needed to generate animal models that develop high incidences of spontaneous malignant tumors with ACI/Seg and Lobund-Wistar rats. It is known that lateral prostate cancer in ACI/Seg rats is most moderately differentiated non-metastatic adenocarcinomas with a cribriform pattern, while prostate cancer in Lobund-Wistar rats is poorly differentiated adenocarcinomas with occasional metastasis.

The present inventors have established rat models of prostate cancer using the followings as carcinogens: N-methyl-N-nitrosourea (MNU); N-nitrosobis (2-oxopropyl) amine (BOP); 3,2'-dimethyl-4-aminobiphenyl (DMAB); and 2-amino-1-methyl-6-phenylimidazo[4,5-b]pyridine (PhIP). The inventors have successfully generated rats developing prostate cancer with high incidence by combining carcinogen administration with the induction of cell proliferation (Jpn. J. Cancer Res., 76: 803–808, 1985). These lesions of prostate cancer were originated in the ventral lobes, and most of them showed a cribriform pattern with no invasion. Their sizes were generally small with no sign of metastasis. Prostate cancers induced by DMAB demonstrated different specificity among the animal species. F344 and ACI rats were the most susceptible, and Wistar and Sprague-Dawley rats showed resistance, yet their histopathological patterns displayed no obvious species specificity.

As in the cases of MNU and BOP, the development of prostate cancer by DMAB can be modified by the long-term and high-dose administration of testosterone propionate (TP). The present inventors subcutaneously implanted TP, which was incorporated into silicon tubes, to raise the serum testosterone concentration to 10-fold and found that the cancer spectrum of the sexual organs of rats that were given DMAB shifted from the ventral lobe to the dorso-lateral and anterior lobes as well as to the testis (Cancer Res., 51:1264–1269, 1991). In contrast to the ventral lobe prostate cancer, the prostate cancer developed in the latter was invasively growing adenocarcinomas with metastatic lesions in the abdominal cavity, liver, lung, and the like. It is also known that the shifting of cancer spectrum from the ventral lobe to the dorso-lateral and anterior lobes and to the testis depends on the dose and duration of TP, and that the degree of their invasiveness depends on the same (Cancer Lett., 83: 11–116, 1994, Jpn. J. Cancer Res., 86:6456–648, 1995).

Molecular studies of cancer induced by carcinogen administration have suggested that Ki-ras gene is involved in the prostate and testis cancers induced by DMAB. Three out of nine adenocarcinomas in the ventral lobe, five out of 13 adenocarcinomas in the dorso-lateral lobe and one out of 11 adenocarcinomas in the testis, demonstrated point mutations in the Ki-ras genes. In contrast, no mutation was found in Ha-ras or p53 genes (Mol. Carcinog., 13:21–26, 1995). There was no difference in the occurrence of ras gene mutation between invasive and non-invasive cancers. Therefore, it is thought that in experimental rat prostate cancers, the activation of the ras protooncogene by point mutation is not associated with the cancer progression and that deactivation of the p53 gene does not correlate with the progression either.

Atypical hyperplasias in the whole regions and the ventral lobe carcinomas are immunohisitochemically androgen receptor-positive, but invasive cancers in the dorso-lateral and anterior lobes are not. Three cell lines established from DMAB plus TP-induced invasive prostate cancer in the dorso-lateral lobes are reported to grow in an androgen-independent manner in vivo (Jpn. J. Cancer Res., 87:1218–1226, 1996, J. Toxicol. Pathol., 11:27–32, 1998). Castration after the treatment with DMAB alone or DMAB plus TP completely arrested the progress of cancers in the ventral lobes that were androgen receptor-positive but it did not terminate the progress of invasive cancers in the dorso-lateral and anterior lobes of the prostate, or in the testes that were androgen receptor-negative (Jpn. J. Cancer Res., 90:23–30, 1999). The recent analysis of the androgen receptor-gene with the use of adenocarcinoma cell lines demonstrated hypermethylation in the promoter region of the receptor, which is thought to be the reason for the androgen-independency of invasive cancers.

Although the induction of prostate cancer through administering carcinogens as described above allows various types of prostate cancers to develop, the animals have to be kept for a long period of one year or more before the development of cancer. Therefore, animal models introduced with cancer-causing genes have been actively generated in recent years. To date, several transgenic animals for prostate cancer have also been reported. Mice, generated by Greenberg in 1995 with the introduction of the probasin promoter of 0.5 kb and the SV40 large T antigen gene, developed prostate cancers that were metastatic. Mice, generated by Barrios in 1996 with the introduction of the probasin promoter of 0.5 kb and ras T24 gene, showed hyperplasias in their prostates but did not develop cancers. Mice, generated by Yan in 1997 with the introduction of the probasin promoter of 11.5 kb and the SV40 large T antigen gene, developed prostate cancers. Mice, generated by Maroulakoou in 1994 with the introduction of the C3 (1) promoter and the SV40 large T antigen gene, developed prostate cancers. Mice, generated by Tehranian in 1996 with the introduction of the C3 (1) promoter and the polyoma middle T gene, developed prostate cancers. Mice, generated by Zhang in 1997 with the introduction of the C3 (1) promoter and the human bcl-2 gene, had hyperplasias in the prostates but did not develop cancers. Mice, generated by Perez-Stable in 1996 with the introduction of the fetal Gγ-globin promoter and the SV40 large T antigen gene, developed prostate cancers. Mice, generated by Kitsberg in 1996, with the introduction of the MMTV promoter and the KGF gene, showed hyperplasias in the prostates but did not develop cancers.

Animal models developing cancers are indispensable both for elucidating the developmental mechanism of cancer and for developing drugs for the treatment. Animal models of various cancers have been generated up to now, but substances and methods for induction of the cancer differ and experimental menu varies depending on animal species used. Therefore, the establishment of model animals of as many species as possible is needed. In this regard, rats are excellent models for acquiring sufficient materials for the analysis because, like mice, the periods for their gestation and sexual maturation are short, they deliver many, something like 10 neonatal rats at one time and because their weight is about 10 times as heavy as mice. In addition to these, rats have many other useful features such as their piled up data concerning chemically caused cancers. However, rat models with the onset of prostate cancer that can surely develop prostate cancer and can be bred for generations stably have not been established. The subject of the present invention is to provide a rat model with the onset of prostate cancer that can develop prostate cancer including invasive cancer and can be bred for generations stably.

DISCLOSURE OF THE INVENTION

The present inventors have made a keen study to solve the subject mentioned above and have found that rat models with the onset of prostate cancer, which can surely develop prostate cancer and can be bred for generations stably, can be established through the following steps: introducing SV40 large T antigen genes that are under the control of probasin gene promoter into rats; breeding the resulting transgenic rats; observing their prostate histopathologically; and selecting the transgenic rat lines in which all the rats develop prostate cancer. Here the inventors have completed the invention.

The present invention relates to: a rat model with the onset of prostate cancer which can develop prostate cancer including invasive cancer and can be bred for generations stably (claim 1); the rat model with the onset of prostate cancer according to claim 1, wherein an SV40 large T antigen gene under the control of probasin gene promoter is introduced (claim 2); the rat model with the onset of prostate cancer according to any of claims 1 or 2, obtained by the steps of: excising an SV40 large T antigen gene (5146-2676) with NcoI and BamHI; then binding it on the downstream of 5'-flanking region (458 bp: from −426 to +32; SEQ ID NO:3) of a rat probasin gene promoter excised with EcoRI and NcoI; introducing the resulting PBSVT transgene of 2944 bp into a fertilized egg of a Sprague-Dawley rat; transplanting the introduced fertilized egg to a recipient rat; and mating a transgenic male rat born from the recipient rat with a wild-type Sprague-Dawley rat (claim 3), the rat model with the onset of prostate cancer according to any of claims 1 to 3, which belongs to a PBSVT transgenic rat 2971 line (claim 4).

The present invention further relates to: a method of establishing a rat model with the onset of prostate cancer which can develop prostate cancer including invasive cancer and can be bred for generations stably, comprising the steps of: excising an SV40 large T antigen gene (5164-2676) with NcoI and BamHI, then binding it on the downstream of 5'-flanking region (458 bp: from −426 to +32) of a rat probasin gene promoter excised with EcoRI and NcoI; introducing the resulting PBSVT transgene of 2944 bp into a fertilized egg of a Sprague-Dawley rat; transplanting the introduced fertilized egg to a recipient rat; mating a transgenic rat born from the recipient rat with a wild-type Sprague-Dawley rat; breeding transgenic offspring rats in a similar manner thereafter; observing the prostate histopathologically; and selecting transgenic rats with the onset of prostate cancer (claim 5); and a method of establishing a rat model with the onset of prostate cancer which can develop prostate cancer including invasive cancer and can be bred for generations stably according to claim 5, which belongs to a PBSVT transgenic rat 2971 line (claim 6).

The present method for a screening method for a substance promoting the onset and/or progress of, or suppressing the onset and/or progress of prostate cancer, wherein a test substance is administered to a rat model with the onset of prostate cancer, before or after the onset of prostate cancer, and wherein the onset and/or progression severity of prostate cancer in said rat model is determined and assessed; the screening method for a substance promoting the onset and/or progress of, or suppressing the onset and/or progress of prostate cancer, wherein the determination and assessment of the onset and/or progression severity of prostate cancer is made by analyzing and assessing histopathological figures of the prostate cancer obtained from a rat model with the onset of prostate cancer; the screening method of a substance promoting the onset and/or progress of, or suppressing the onset and/or progress of prostate cancer, wherein the determination and assessment of the onset and/or progression severity of prostate cancer is the determination and assessment of prostanoic acid phosphatase (PAP) and/or a prostate-specific antigen (PSA) produced in prostate cancer cells; the screening method of a substance promoting the onset and/or progress of, or suppressing the onset and/or progress of prostate cancer, wherein the determination level of a wild-type rat of the same species as the rat model with the onset of prostate cancer is used for comparison and assessment, when determining and assessing the onset and/or progression severity of prostate cancer; a substance promoting the onset and/or progress of prostate cancer obtained by the screening method of a substance promoting the onset and/or progress of, or suppressing the onset and/or progress of prostate cancer; a substance suppressing the onset and/or progress of prostate cancer obtained by the screening method of a substance promoting the onset and/or progress of, or suppressing the onset and/or progress of prostate cancer; the substance suppressing the onset and/or progress of prostate cancer, wherein said substance is a drug to prevent, to suppress or to treat the prostate cancer; and a pharmaceutical composition used to treat a patient in need of suppressing the onset and/or progress of prostate cancer, wherein said pharmaceutical composition comprises, as an active ingredient, the substance suppressing the onset and/or progress of prostate cancer.

BEST MODE TO CARRY OUT THE INVENTION

Any rat line can be a rat model with the onset of prostate cancer of the present invention as long as it can develop prostate cancer including an invasive cancer in almost all the rats and can be bred for generations stably. A rat model with the onset of prostate cancer, including PBSVT transgenic rat 2971 line, exemplifies a rat model developing prostate cancer which is established from a transgenic rat introduced with a transgene (PBSVT transgene) to which SV40 large T antigen gene is bound. The SV40 large T antigen gene is expressed specifically in the prostate, and induces cancer by inactivating p53 and Pb proteins by directly binding to them under the control of probasin gene encoding androgen- or zinc-regulated proteins.

The method of establishing a rat model with the onset of prostate cancer of the present invention can be exemplified with previously known methods of generating transgenic animals (for instance, Proc. Natl. Acad. Sci. USA77: 7380–7384, 1980). The method of the invention will be described below with an example of the case wherein a gene fragment, in which the SV40 large T antigen gene is positioned under the foregoing probasin promoter control, is used as a transgene. A PBSVT transgene prepared according to the previously known method is amplified in an appropriate expression vector and gene fragments (PBSVT transgenes) are excised after the amplification. These PBSVT transgenes are introduced into rat fertilized eggs in the pronuclear stage by microinjection and the post-introduction fertilized eggs are transplanted to recipient rats, and neonatal rats are obtained. DNA is extracted from part of the bodies (for example, tips of the tails) for southern blotting analysis or PCR assay and so on, to confirm whether the neonatal rats are introduced with PBSVT transgenes. Individuals confirmed to have the PBSVT transgene are the founders, which are then mated with normal wild type rats. 50% of the obtained neonates (F1) inherit the PBSVT transgene. These F1 rats that are confirmed the introduction of the PBSVT transgene are mated with normal rats, and the procedure goes on likewise, while observing the histopathology of the prostates and selecting transgenic rats that develop prostate cancer. A rat model line for developing prostate cancer can thus be established.

A promoter derived from a prostate specific antigen (PSA) or a prostate specific membrane antigen (PSMA) which is specifically expressed in the prostate can be also used for the foregoing transgene instead of the probasin gene promoter. SV40 large T antigen gene, which induces cancer, can be substituted with the large T antigen gene of SV40 thermosensitive mutant line tsA58, EIA gene of adenovirus, HPV16 gene of human Papilloma virus and the like. Further, Electric Pulse, Liposome, Calcium phosphate methods and so on can be conducted instead of the above-mentioned microinjection for an introducing method of fertilized eggs.

The above-mentioned PBSVT transgenic rat 2971 line, the rat model of the present invention for developing prostate cancer, which is created as a rat model with the onset of prostate cancer capable of developing prostate cancer including an invasive cancer and capable of breeding for generations stably, is established by the following steps: excising the SV40 large T antigen gene (5164-2676) with NcoI and BamHI, then binding it on the downstream of 5'-flanking region (458 bp: from −426 to +32) of the rat probasin gene promoter excised with EcoRI and NcoI; introducing the resulting PBSVT transgene of 2944 bp into a fertilized egg of a Sprague-Dawley rat; after the introduction, transplanting the fertilized egg to a recipient rat; mating a transgenic rat born from the recipient rat with a wild-type Sprague-Dawley rat; breeding transgenic offspring rats obtained in a similar manner thereafter; observing the prostates histopathologically; and selecting transgenic rats that developed prostate cancers. The PBSVT transgenic rat 2971 line is maintained at the $1^{st}$ Department of Pathology, Nagoya City University Medical School, where the rats of this line are available under certain conditions for those concerned.

The rat model of the present invention with the onset of prostate cancer as described above can be used not only for elucidating the developmental mechanism of prostate cancer but for screening any substance to promote or suppress the prostate cancer development and progression, and so forth. These screening methods, for example, include a method of determining and assessing the onset and/or the progression severity of prostate cancer in the rat models with the onset of prostate cancer of the present invention, wherein a test substance is administered to the rat models before or after their cancer development. A determining and assessing method of the onset and/or the progression severity of prostate cancer is exemplified by a method wherein the histopathological figures of prostate cancer obtained from the rat models administered with a test substance is analyzed and assessed. When determining and assessing the onset and/or the progression severity of prostate cancer, it is preferable to use simultaneously wild type rats of the same line as a rat model with the onset of prostate cancer as this will make comparative experiments accurate on individual levels.

A substance suppressing the onset and/or the progress of prostate cancer obtained by the screening method of the present invention provides possibility for its use as a preventive drug, a suppressing drug, a treatment, or the like for prostate cancer. For instance, when performing the screening method mentioned above, administration of a test substance before the development of the prostate cancer is suitable for the screening of a preventive drug for the prostate cancer. On the contrary, administration of a test substance after the development of the prostate cancer is suitable for the screening of a drug for the treatment and for amelioration of the symptoms of the prostate cancer. On the other hand, a substance promoting the onset and/or the progress of prostate cancer is thought to be useful to give rise to the prostate cancer to the sufficient level in an animal model with the poor development of prostate cancer. In addition, a pharmaceutical composition of the present invention for the treatment of a patient in need of suppressing the onset and/or the progress of prostate cancer contains a substance for suppressing the onset and/or the progress of prostate cancer, as an active ingredient, together with publicly known substances necessary for the drug preparation.

The present invention will be explained below based on the examples but the invention will not be limited to these examples.

(Construction of the PBSVT Transgene)

Figure 1:
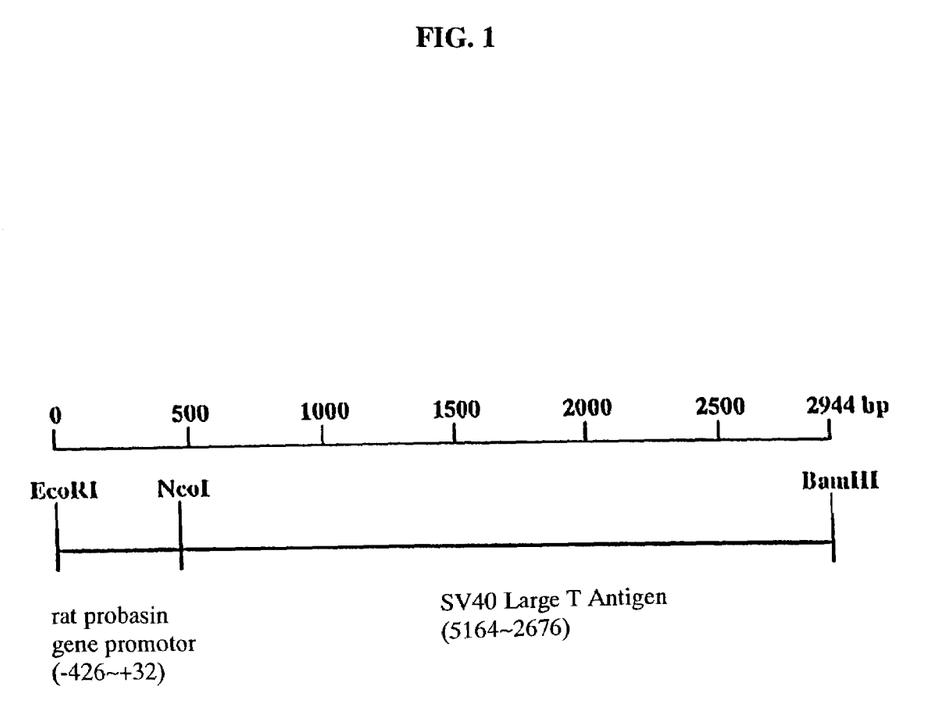
FIG. 1 shows a fragment of PBSVT gene used to generate a transgenic rat model of prostate cancer of the present invention.

SV40 large T antigen gene used was the gene incorporated as the NcoI-BamHI fragment into the multi-cloning site of pBluescriptIIKS(−) which was provided by Human Science Research Resources Bank. The above SV40 large T antigen gene (5164-2676) excised with NcoI and BamHI from the pBluescriptIIKS(−) was ligated on the downstream of 5'-flanking region (458 bp: from −426 to +32) of the rat probasin gene promoter excised with EcoRI and NcoI, thus the PBSVT transgene was constructed (FIG. 1). The PBSVT transgene that can express both SV40 large T antigen of 2944 bp and the small t antigen was digested with restriction enzymes, EcoRI and BamHI, after having been amplified with plasmid pBluescriptII (Transgene). The transgenes then underwent 1% agarose gel electrophoresis to have the plasmid parts removed and were separated for linearized DNA fragments. Then these linearized DNA fragments were collected using GENE CLEANE II (BIO 101 INC) and the DNA obtained after this purification was dissolved in the injection buffer (10 mM Tris-HCl including 0.1 mM EDTA, pH7.6) to 5 µg/ml and kept at −20° C. until manipulated for injection.

(Generation of the Transgenic Rat)

The PBSVT transgene solution described above was microinjected into rat fertilized eggs in the pronuclear stage according to the following protocol. 8-week-old Sprague-Dawley (SD) female rats were fed under 12-hour cycles of light and dark (light hours 4:00–16:00), temperature at about 23° C. and moisture of about 55%. Then vaginal smear test was conducted to observe sexual cycles of the female rats and to select the day for the hormone treatment. 150 IU/kg of pregnant mare's serum gonadotropin (NIPPON ZENYAKU; "PMS ZENYAKU") was intraperitoneally administered to the female rats for superovulation, and 48 hours thereafter, 75 IU/kg of human chorionic gonadotropin (SANKYO ZOKI; "Puberogen") was administered. The female rats were then co-resided with males for mating. After 32 hours of human chorionic gonadotropin administration, fertilized eggs in the pronuclear stage were collected through oviduct perfusion. The mKRB solution (Y. Yoshida and M. C. Chang, J. Reprod. Fertil., Vol. 36, pp9–22(1974)) was used for the oviduct perfusion and egg cultivation. The collected fertilized eggs were enzymatically treated for 5 minutes at 37° C. in the mKRB solution supplemented with 0.1% hyaluronidase (Sigma) to remove the cumulus oophorus cells. The fertilized eggs were then washed three times in the mKRB solution to remove the enzyme and were kept in a $CO_2$ incubator ($CO_2$ 5%, 37° C., saturated moisture) until manipulated for DNA injection. Male pronulceus of Wistar rat fertilized eggs prepared as described above were introduced with the foregoing PBSVT transgene solution to 10 molecules per one fertilized egg. 200 fertilized eggs introduced with the solution were transplanted to 10 recipient rats and 40 neonates were given birth. DNA prepared from the tails just after weaning were analyzed by PCR method with primers according to Seq. ID Nos.1 and 2 on the sequence listing. The result proved that four founder (F0) male transgenic rats of SD line were generated.

These founder male transgenic rats were mated with normal wild-type female rats of SD line to create the first filial generation (F1) and the time-course pathological changes occurring in the systemic organs were studied. Two rats of 2944 and 2971 lines among four transgenic rats were found capable for establishing their lines. Rats of 2971 line can be bred for generations stably and are thereby successfully established as PBSVT transgenic rats. On the contrary, rats of 2944 line, as breeding continue, suffered frequent developments of hydrocephalus and the line became extinct.

Paralysis in both hind limbs appeared in F0 rats of 2944 and 2971 lines at around 12 weeks of age and they died at weeks 14 and 25. Marked atypical hyperplasias were diffusively found in the prostate ventral lobes in both lines but no cancer lesions were observed. SV40 T antigen was expressed in all prostate lobes and was expressed frequently in the ventral lobe in particular. Bone tumors of the spine were observed in both the lines and further hypoglossal tumors were also found in 2971 line. All of the tumors were malignant small round cell tumors and positive for the SV40 T antigen. General observation with regard to those dead and killed in the process of breeding of 2971 and 2944 lines are shown in Table 1, "General observation of PBSVT transgenic rats of 2971 line (cases for dead or killed)" and in Table 2, "General observation of PBSVT transgenic rats of 2944 line (cases for dead or killed)". In addition to these, the histopathological findings in their prostates are shown in Table 3, "Histopathological findings in the PBSVT transgenic rat prostates". As shown in Table 1, 2971 line rats are confirmed to be capable for breeding. Parvocellular undifferentiated malignant tumors were found to develop in tongues and the proximal of spinal cords other than in their prostates. In addition, many individuals of 2944 line rats died of hydrocephalus as indicated in Table 2. Other than in prostates, parvocellular undifferentiated malignant tumors were developed in tongues, the proximal of spinal cords, and the like.

TABLE 1

General observation of PBSVT transgenic rats of 2971 line (cases for dead or killed)

| Animal No. | | Sex | Weeks of age | Dead or killed | General observation |
|---|---|---|---|---|---|
| F0 | | M | 25 | dead | Tumors in spinal cord, tongue and lymph node |
| F1 | 27 | F | 26 | dead | Tumors in spinal cord, tongue and lymph node |
| | 28 | M | 3 | killed | — |
| | 31 | F | 26 | dead | Tumors in spinal cord, tongue and lymph node |
| | 34 | F | 26 | killed | Tumors in spinal cord, tongue and lymph node |
| | 55 | M | 17 | dead | Tumor in spinal cord |
| | 56 | M | 22 | dead | Tumors in spinal cord, tongue and lymph node |
| | 59 | M | 24 | killed | Tumors in spinal cord, tongue and lymph node |
| | 61 | M | 15 | dead | Tumors in spinal cord, tongue and lymph node |
| | 62 | M | 16 | dead | Tumors in spinal cord, tongue and lymph node |
| | 66 | F | 19 | dead | Tumors in spinal cord, tongue and lymph node |
| | 69 | F | 13 | dead | Tumors in tongue and lymph node |
| | 70 | F | 25 | killed | Tumors in spinal cord, tongue and lymph node |
| | 75 | M | 24 | dead | Tumors in spinal cord, tongue and lymph node |
| | 76 | M | 19 | dead | Tumors in spinal cord, tongue and lymph node |
| | 77 | F | 21 | dead | Tumors in spinal cord, tongue and lymph node |
| | 78 | F | 24 | dead | Tumors in spinal cord, tongue and lymph node |
| | 79 | F | 24 | dead | Tumors in tongue and lymph node |

TABLE 1-continued

General observation of PBSVT transgenic rats of 2971 line (cases for dead or killed)

| Animal No. | Sex | Weeks of age | Dead or killed | General observation |
|---|---|---|---|---|
| 81 | F | 25 | killed | Tumors in spinal cord, tongue and lymph node |
| 84 | M | 25 | dead | Tumors in tongue and lymph node |
| 100 | F | 21 | dead | Tumors in spinal cord, tongue and lymph node |
| 102 | M | 17 | dead | Tumors in spinal cord, tongue and lymph node |
| 104 | M | 15 | dead | Tumors in spinal cord, tongue and lymph node |
| 105 | M | 20 | killed | — |

TABLE 2

General observation of PBSVT transgenic rats of 2944 line (cases for dead or killed)

| | Animal No. | Sex | Weeks of age | Dead or killed | General observation |
|---|---|---|---|---|---|
| F0 | | M | 14 | dead | Tumor in spinal cord |
| F1 | 4 | M | 15 | dead | Tumors in spinal cord, tongue and lymph node |
| | 7 | F | 17 | dead | Tumors in spinal cord, tongue, thyroid gland and lymph node |
| | 8 | F | 18 | dead | Tumors in spinal cord, tongue and lymph node |
| | 9 | M | 4 | killed | hydrocephalus |
| | 17 | F | 4 | killed | hydrocephalus |
| | 18 | F | 19 | dead | Tumors in spinal cord, tongue and lymph node |
| | 19 | F | 19 | dead | Tumors in spinal cord, tongue and lymph node |
| | 20 | F | 16 | dead | Tumors in spinal cord, tongue and lymph node |
| F2 | 120 | M | 3 | killed | hydrocephalus |
| | 121 | M | 3 | killed | hydrocephalus |
| | 122 | M | 3 | killed | hydrocephalus |
| | 125 | F | 14 | dead | hydrocephalus, tumors in tongue, thyroid gland and lymph node |
| | 126 | F | 14 | dead | hydrocephalus, tumors in tongue and lymph node |
| | 129 | F | 15 | dead | hydrocephalus, tumors in spinal cord, tongue and lymph node |
| | 130 | F | 7 | dead | hydrocephalus |
| | 133 | M | 9 | dead | hydrocephalus |
| | 139 | F | 18 | dead | Tumors in spinal cord, tongue and lymph node |
| | 142 | F | 4 | dead | hydrocephalus |
| | 145 | M | 15 | killed | hydrocephalus, tumors in tongue, thyroid gland and lymph node |
| | 146 | M | 15 | killed | hydrocephalus, tumors in tongue, thyroid gland and lymph node |

TABLE 3

Histopathological findings in the PBSVT transgenic rat prostates

| | Animal No. | Line | Weeks of age | Prostate Compound lobe | Prostate Dorso-lateral lobe | Prostate Anterior lobe |
|---|---|---|---|---|---|---|
| F0 | | 2944 | 14 | AH | AH | n.p. |
| F1 | 4 | 2944 | 15 | AH | AH | n.p. |
| | 9 | 2944 | 4 | n.p. | n.p. | n.p. |
| | 145 | 2944 | 15 | AH | — | — |
| | 146 | 2944 | 15 | AH | — | — |
| F0 | | 2971 | 25 | Atrophy | Atrophy | — |
| F1 | 28 | 2971 | 3 | n.p. | n.p. | n.p. |
| | 55 | 2971 | 17 | Atrophy | Atrophy | CA |
| | 56 | 2971 | 22 | Atrophy | Atrophy | — |
| | 59 | 2971 | 24 | Atrophy | — | — |
| | 62 | 2971 | 16 | Atrophy | Atrophy | — |
| | 104 | 2971 | 15 | — | AH | CA |

AH: atypical hyperplasias
CA: cancer
n.p.: no practice

Five 2971 line PBSVT transgenic rats, 15 weeks of age, were killed for histopathological examination of the prostate and testis. The examination revealed that each prostate lobe developed adenocarcinomas in almost all the cases that were atypical tumor cells arranged in a glandular structure accompanied by many mitotic figures. Particularly in the anterior lobe, invasive cancers were observed to develop. The results are shown in Table 4 "Histopathological findings in PBSVT transgenic rat prostates and testes".

TABLE 4

Histopathological findings of PBSVT transgenic rat prostates and testes

| | Number of rats | Compound lobe | | Dorsal lobe | | Lateral lobe | | Anterior lobe | | Testis | |
|---|---|---|---|---|---|---|---|---|---|---|---|
| | | AH | Ca | AH | Ca | AH | Ca | AH | Ca | AH | Ca |
| 15 week-old | 5 | 5 | 4 (0) | 5 | 2 (0) | 5 | 4 (0) | 5 | 5 (5) | 0 | 0 |

AH: atypical hyperplasias
CA: cancer
( ): invasive cancer

Immunohistochemical observation of PBSVT transgenic rats for the protein expression of SV40 large T antigen revealed that the expression was found in each lobe of the prostates, in the salivary gland ducts, and in the testis Sertoli cells. The results are shown in Table 5, "Immunohistochemical observation results for the protein expression of SV40 large T antigen in PBSVT transgenic rats".

TABLE 5

Immunohistochemical observation results for the protein expression of SV40 large T antigen in PBSVT transgenic rats

| Prostate | |
|---|---|
| Compound lobe | ++ |
| Dorsal lobe | ++ |
| Lateral lobe | ++ |
| Anterior lobe | + |
| Testis | − |
| Testis (Spermary) | |
| Sertoli cell | ± |
| Epididymis | − |
| Lung | − |
| Salivaly gland | |
| Duct cell | ± |
| Acinous cell | − |
| Colon | − |
| Liver | − |
| Pancreas | − |
| Thymus | − |
| Lymph node | − |
| Cerebrum | − |
| Cerebellum | − |

++: intensively positive
+: moderately positive
±: poorly positive
−: negative

The experiment as described below was conducted to study the effect of the testosterone administration on the development of cancer.

Male PBSVT transgenic rats were grouped into three at five weeks of age. The first group served as the control group, the second underwent castration, and into the rats of the third group, testosterone filled in 1.5 cm Silicon tubes was subcutaneously transplanted. Transgenic rats of all three groups were killed at 15 weeks of age and their pathological changes in the prostate were histopathologically examined. All controls of the first group displayed marked atypical hyperplasias diffusively in the anterior lobes of the prostate and some of them developed cancer. In the second group, prostates generally displayed atrophy with no sign of neoplastic lesions. In the third group, the entire prostates showed considerable swelling with the high incidence of invasive cancers. However, castration after the testosterone administration for a duration of 15 weeks resulted in involution of the prostate and all of the proliferative lesions disappeared. These findings revealed that the prostate tumor development in the PBSVT transgenic rats is androgen-dependent and testosterone administration will progress their prostate tumors in a short period and considerably. In addition, prostate cancers were proved to develop by inactivating p53 and Pb proteins.

INDUSTRIAL APPLICABILITY

These animal models allow prostate cancer to develop at early stages with high incidence. Therefore, they are quite useful prostate cancer models for analyzing the developmental process of prostate cancers in detail and for developing drugs for the treatment of prostate cancer. The characteristics of transgenic rats of the present invention show that they are useful in the field of medical research.

What is claimed is:

1. A transgenic rat model with the onset of prostate cancer, wherein the genome of the transgenic rat model comprises a 2944 bp PBSVT transgene consisting of the nucleic acid sequence of the SV40 large T antigen, operably linked to a 458 bp nucleic acid sequence of the probasin gene promoter of SEQ ID NO:3, wherein the SV40 large T antigen is expressed in the prostate glands of said transgenic rat and where the transgenic rat develops prostate cancer including invasive cancer.

2. A method of making a transgenic rat model with the onset of prostate cancer, comprising:
(i) making a 2944 bp PBSVT transgene consisting of the nucleic acid sequence of the SV40 large T antigen, operably linked to a 458 bp nucleic acid sequence of the probasin gene promoter of SEQ ID NO:3,
(ii) transfecting a fertilized egg of a Sprague-Dawley rat with said PBSVT transgene,
(iii) impregnating a female Sprague-Dawley rat with said fertilized egg of a Sprague-Dawley rat,
(iv) breeding offspring of the said fertilized egg of a Sprague-Dawley rat with a wild-type Sprague-Dawley rat to obtain F1 progeny that are heterozygous for the said PBSVT transgene,
(v) breeding said F1 progeny to obtain F2 offspring that are homozygous for the said PBSVT transgene,
(vi) selecting male rats with the onset of prostate cancer, including invasive cancer on the basis of observed histopathological changes to the prostate.

3. A screening method for a substance promoting the onset and/or progress of, or suppressing the onset and/or progress of prostate cancer, wherein a test substance is administered to a rat model according to claim 1, before or after the onset of prostate cancer, and wherein the onset and/or progression severity of prostate cancer in said rat model is determined and assessed.

4. The screening method for a substance promoting the onset and/or progress of, or suppressing the onset and/or progress of prostate cancer according to claim 3, wherein the determination and assessment of the onset and/or progression severity of prostate cancer is made by analyzing and assessing histopathological figures of prostate cancer obtained from the rat model.

5. The screening method of a substance promoting the onset and/or progress of, or suppressing the onset and/or progress of prostate cancer according to claim 3, wherein the determination and assessment of the onset and/or progression severity of prostate cancer is the determination and assessment of prostanoic acid phosphatase (PAP) and/or a prostate-specific antigen (PSA) produced in prostate cancer cells.

6. The screening method of a substance promoting the onset and/or progress of, or suppressing the onset and/or progress of prostate cancer according to claim 4, wherein the determination and assessment of the onset and/or progression severity of prostate cancer is made by analyzing and assessing histopathological figures of prostate cancer obtained from a wild-type rat of the same species as the rat model for comparison and assessment, when determining and assessing the onset and/or progression severity of prostate cancer.

7. The screening method of a substance promoting the onset and/or progress of, or suppressing the onset and/or progress of prostate cancer according to claim 5, wherein the level of prostanoic acid phosphatase PAP and/or a prostate-specific antigen PSA is determined and assessed for a wild-type rat of the same species as the rat model and compared to said rat model with the onset of prostate cancer.

\* \* \* \* \*

SEQUENCE LISTING

<160> NUMBER OF SEQ ID NOS: 4

<210> SEQ ID NO 1
<211> LENGTH: 20
<212> TYPE: DNA
<213> ORGANISM: Artificial

-continued

```
<220> FEATURE:
<223> OTHER INFORMATION: Description of Artificial Sequence:Primer

<400> SEQUENCE: 1
gtcagcagta gcctcatcat                                                   20

<210> SEQ ID NO 2
<211> LENGTH: 20
<212> TYPE: DNA
<213> ORGANISM: Artificial
<220> FEATURE:
<223> OTHER INFORMATION: Description of Artificial Sequence:Primer

<400> SEQUENCE: 2
ggttgattgc tactgcttcg                                                   20

<210> SEQ ID NO 3
<211> LENGTH: 458
<212> TYPE: DNA
<213> ORGANISM: Rattus norvegicus

<400> SEQUENCE: 3
agcttccaca agtgcattta gcctctccag tattgctgat gaatccacag ttcaggttca       60
atggcgttca aaacttgatc aaaaatgacc agactttata ttcttacacc aacatctatc     120
tgattggagg aatggataat agtcatcatg tttaaacatc taccattcca gttaagaaaa     180
tatgatagca tcttgttctt agtctttttc ttaataggga cataaagccc acaaataaaa     240
atatgcctga agaatgggac aggcattggg cattgtccat gcctagtaaa gtactccaag     300
aacctatttg tatactagat gacacaatgt caatgtctgt gtacaactgc caactgggat     360
gcaagacact gcccatgcca atcatcctga aaagcagcta taaaaagcag gaagctactc     420
tgcaccttgt cagtgaggtc cagataccta cagagctc                             458

<210> SEQ ID NO 4
<211> LENGTH: 2471
<212> TYPE: DNA
<213> ORGANISM: Simian virus 40

<400> SEQUENCE: 4
acaattgcat tcattttatg tttcaggttc aggggaggt gtgggaggtt ttttaaagca       60
agtaaaacct ctacaaatgt ggtatggctg attatgatca tgaacagact gtgaggactg     120
aggggcctga atgagccttt gggactgtga atcaatgcct gtttcatgcc ctgagtcttc     180
catgttcttc tccccaccat cttcattttt atcagcattt tcctggctgt cttcatcatc     240
atcatcactg tttcttagcc aatctaaaac tccaattccc atagccacat taaacttcat     300
tttttgatac actgacaaac taaactcttt gtccaatctc tctttccact ccacaattct     360
gctctgaata ctttgagcaa actcagccac aggtctgtac caaattaaca taagaagcaa     420
agcaatgcca ctttgaatta ttctcttttc taacaaaaac tcactgcgtt ccaggcaatg     480
ctttaaataa tctttgggcc taaaatctat ttgttttaca aatctggcct gcagtgtttt     540
aggcacactg tactcattca tggtgactat tccaggggga atatttgag ttcttttatt      600 taggtgtttc ttttctaagt ttaccttaac actgccatcc aaataatccc ttaaattgtc     660
caggttatta attccctgac ctgaaggcaa atctctggac tcccctccag tgcccttttac    720 atcctcaaaa actactaaaa actggtcaat agctactcct agctcaaagt tcagcctgtc     780
caagggcaaa ttaacattta agctttccc cccacataat tcaagcaaag cagctgctaa      840
```

-continued

```
tgtagtttta ccactatcaa ttggtcctttt aaacagccag tatcttttt taggaatgtt      900
gtacaccatg cattttaaaa agtcatacac cactgaatcc attttgggca acaaacagtg      960
tagccaagca actccagcca tccattcttc tatgtcagca gagcctgtag aaccaaacat     1020
tatatccatc ctatccaaaa gatcattaaa tctgtttgtt aacatttgtt ctctagttaa     1080
ttgtaggcta tcaacccgct ttttagctaa aacagtatca acagcctgtt ggcatatggt     1140
tttttggttt ttgctgtcag caaatatagc agcatttgca taatgctttt catggtactt     1200
atagtggctg ggctgttctt ttttaataca ttttaaacac atttcaaaac tgtactgaaa     1260
ttccaagtac atcccaagca ataacaacac atcatcacat tttgtttcca ttgcatactc     1320
tgttacaagc ttccaggaca cttgtttagt ttcctctgct tcttctggat taaaatcatg     1380
ctcctttaac ccacctggca aactttcctc aataacagaa aatggatctc tagtcaaggc     1440
actatacatc aaatattcct tattaaccc tttacaaatt aaaaagctaa aggtacacaa     1500
ttttttgagca tagttattaa tagcagacac tctatgcctg tgtggagtaa gaaaaaacag     1560
tatgttatga ttataactgt tatgcctact tataaaggtt acagaatatt tttccataat     1620
tttcttgtat agcagtgcag ctttttcctt tgtggtgtaa atagcaaagc aagcaagagt     1680
tctattacta aacacagcat gactcaaaaa acttagcaat tctgaaggaa agtccttggg     1740
gtcttctacc tttctcttct ttttggagg agtagaatgt tgagagtcag cagtagcctc     1800
atcatcacta gatggcatt cttctgagca aaacaggttt tcctcattaa aggcattcca     1860
ccactgctcc cattcatcag ttccataggt tggaatctaa aatacacaaa caattagaat     1920
cagtagttta acacattata cacttaaaaa ttttatattt accttagagc tttaaatctc     1980
tgtaggtagt ttgtccaatt atgtcacacc acagaagtaa ggttccttca caaagatcaa     2040
gtccaaacca cattctaaag caatcgaagc agtagcaatc aacccacaca agtggatctt     2100
tcctgtataa ttttctattt tcatgcttca tcctcagtaa gcacagcaag catatgcagt     2160
tagcagacat tttctttgca cactcaggcc attgtttgca gtacattgca tcaacaccag     2220
gatttaagga agaagcaaat acctcagttg catcccagaa gcctccaaag tcaggttgat     2280
gagcatattt tactccatct tccattttct tgtacagagt attcattttc ttcatttttt     2340
cttcatctcc tccttatca ggatgaaact ccttgcattt ttttaaatat gcctttctca     2400
tcagaggaat attccccag gcactccttt caagacctag aaggtccatt agctgcaaag     2460
attcctctct g                                                          2471
```